(12) United States Patent
Yun

(10) Patent No.: US 11,883,172 B2
(45) Date of Patent: Jan. 30, 2024

(54) ELECTRONIC DEVICE FOR GENERATING HEALTH INFORMATION ON BASIS OF PLURALITY OF BIOSIGNALS AND OPERATION METHOD THEREFOR

(71) Applicant: Samsung Electronics Co., Ltd., Suwon-si (KR)

(72) Inventor: Inho Yun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 743 days.

(21) Appl. No.: 16/964,031

(22) PCT Filed: Jan. 22, 2019

(86) PCT No.: PCT/KR2019/000917
§ 371 (c)(1),
(2) Date: Jul. 22, 2020

(87) PCT Pub. No.: WO2019/151701
PCT Pub. Date: Aug. 8, 2019

(65) Prior Publication Data
US 2021/0038141 A1     Feb. 11, 2021

(30) Foreign Application Priority Data

Feb. 2, 2018  (KR) ........................ 10-2018-0013639

(51) Int. Cl.
*A61B 5/16* (2006.01)
*H04B 17/318* (2015.01)
(Continued)

(52) U.S. Cl.
CPC ............ *A61B 5/165* (2013.01); *A61B 5/0002* (2013.01); *A61B 5/0059* (2013.01); *A61B 5/05* (2013.01);
(Continued)

(58) Field of Classification Search
None
See application file for complete search history.

(56) References Cited

U.S. PATENT DOCUMENTS

2008/0009685 A1    1/2008  Kim et al.
2009/0203972 A1    8/2009  Heneghan et al.
(Continued)

FOREIGN PATENT DOCUMENTS

JP    2016-144560 A    8/2016
JP    2017-127371 A    7/2017
(Continued)

OTHER PUBLICATIONS

Korean Office Action dated Feb. 25, 2022, issued in Korean Application No. 10-2018-0013639.
(Continued)

*Primary Examiner* — Lynsey C Eiseman
*Assistant Examiner* — Amanda L Steinberg
(74) *Attorney, Agent, or Firm* — Jefferson IP Law, LLP

(57) ABSTRACT

An electronic device may determine whether a user wears the electronic device by means of at least one sensor; measure a first bio-signal of the user by means of the at least one sensor while the user wears the electronic device; drive an RF sensor included in a charging device while the electronic device is connected to the charging device including the RF sensor through an interface, thereby measuring a second bio-signal of the user that is generated by the RF signal oscillated from the RF sensor; receive at least one of electric power for charging the battery from the charging device and the second bio-signal through the interface; generate health information of the user on the basis of at least the first bio-signal and the second bio-signal; and display the generated health information on a display.

16 Claims, 11 Drawing Sheets

(51) Int. Cl.
  *A61B 5/00*      (2006.01)
  *A61B 5/05*      (2021.01)
  *A61B 5/08*      (2006.01)
  *A61B 5/11*      (2006.01)
  *G08B 21/18*     (2006.01)
  *H02J 7/00*      (2006.01)

(52) U.S. Cl.
  CPC .......... *A61B 5/0816* (2013.01); *A61B 5/1126* (2013.01); *A61B 5/486* (2013.01); *A61B 5/4809* (2013.01); *A61B 5/6844* (2013.01); *A61B 5/742* (2013.01); *A61B 5/7475* (2013.01); *G08B 21/18* (2013.01); *H04B 17/318* (2015.01); *A61B 2560/0214* (2013.01); *A61B 2560/0242* (2013.01); *H02J 7/0042* (2013.01)

(56) References Cited

U.S. PATENT DOCUMENTS

| | | |
|---|---|---|
| 2011/0178377 A1 | 7/2011 | Heneghan et al. |
| 2011/0234152 A1* | 9/2011 | Frossen ................. H02J 7/0044 320/107 |
| 2015/0269824 A1* | 9/2015 | Zhang .................... A61B 5/746 340/539.12 |
| 2016/0058366 A1 | 3/2016 | Choi et al. |
| 2016/0151603 A1 | 6/2016 | Shouldice et al. |
| 2016/0195856 A1* | 7/2016 | Spero ................... H05B 47/155 700/90 |
| 2016/0310046 A1 | 10/2016 | Heinrich et al. |
| 2016/0335401 A1 | 11/2016 | Kawai et al. |
| 2017/0011210 A1 | 1/2017 | Cheong et al. |
| 2017/0136348 A1* | 5/2017 | Hattori .................. G16H 10/20 |
| 2020/0297955 A1* | 9/2020 | Shouldice ............. G16H 40/63 |
| 2021/0150873 A1* | 5/2021 | Shouldice .......... G08B 21/0469 |

FOREIGN PATENT DOCUMENTS

| | | |
|---|---|---|
| KR | 10-2015-0099430 A | 8/2015 |
| KR | 10-2016-0024627 A | 3/2016 |
| WO | 2016/021236 A1 | 2/2016 |

OTHER PUBLICATIONS http://blog.naver.com/leesujae17/220867955360 Nov. 22, 2016.
European Search Report dated Dec. 22, 2020, issued in European Application No. 19747606.2.

* cited by examiner

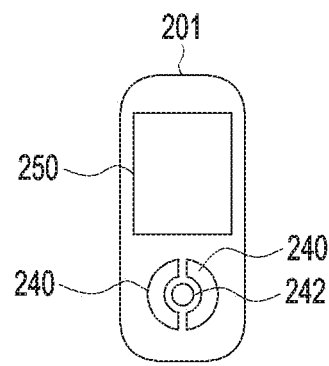
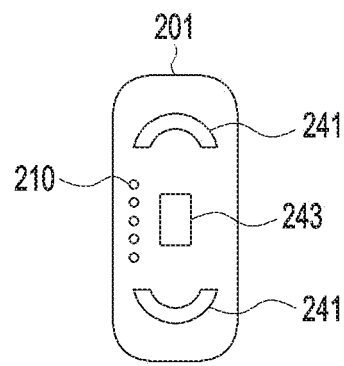
FIG.2A  FIG.2B
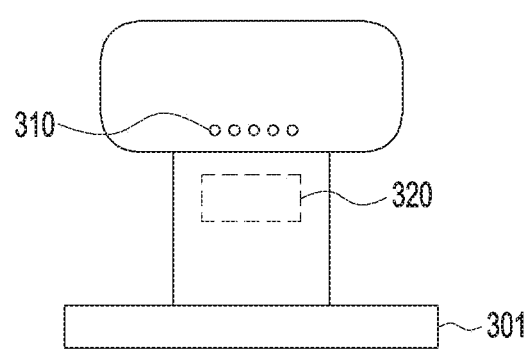
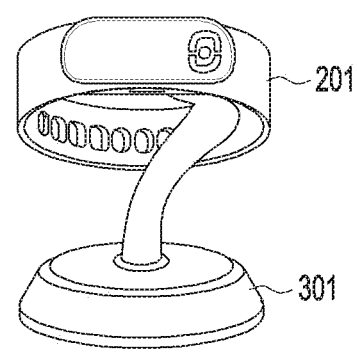
FIG.3A  FIG.3B

ELECTRONIC DEVICE FOR GENERATING HEALTH INFORMATION ON BASIS OF PLURALITY OF BIOSIGNALS AND OPERATION METHOD THEREFOR

CROSS-REFERENCE TO RELATED APPLICATION(S)

This application is a U.S. National Stage application under 35 U.S.C. § 371 of an International application number PCT/KR2019/000917, filed on Jan. 22, 2019, which is based on and claimed priority of a Korean patent application number 10-2018-0013639, filed on Feb. 2, 2018, in the Korean Intellectual Property Office, the disclosure of which is incorporated by reference herein in its entirety.

BACKGROUND

1. Field

Various embodiments of the disclosure relate to an electronic device for generating health information on the basis of a plurality of bio-signals, and an operation method therefor.

2. Description of the Related Art

Various electronic devices that can be worn on the body of a user have been developed. Wearable electronic devices may include various sensors. For example, an electronic device may include various sensors such as an acceleration sensor, a gyro sensor, a temperature-humidity sensor, a proximity sensor, and an optical sensor. A user can measure information related to the body of the user through various sensors while wearing the electronic device, and identify his/her body.

SUMMARY

Although information related to the body is required to be continuously measured, an electronic device is required to be charged in order to operate while being worn on the body of a user. In addition, the user has inconvenience in always wearing a wearable electronic device.

An electronic device according to various embodiments of the disclosure can measure bio-information of a user by using a sensor included in the electronic device while the user is wearing the electronic device, and measure bio-information of the user by using a sensor included in a charging device during charging of the electronic device while the user is not wearing the electronic device.

An electronic device according to various embodiments of the disclosure, which is a wearable electronic device, can measure bio-information generated while a user is sleeping by using a sensor included in a charging device on which the wearable electronic device is mounted to be charged, without requiring the user to wear the wearable electronic device while sleeping.

An electronic device according to various embodiments may include: a battery; a display; at least one sensor; an interface; at least one memory; and at least one processor electrically connected to the display, the at least one sensor, and the at least one memory, wherein the at least one processor is configured to: determine whether a user is wearing the electronic device, by using the at least one sensor; measure a first bio-signal of the user by using the at least one sensor while the user is wearing the electronic device; while the electronic device is connected to a charging device including an RF sensor through the interface, drive the RF sensor included in the charging device, and measure a second bio-signal of the user, the second bio-signal being generated by an RF signal oscillated from the RF sensor; receive at least one of the second bio-signal and power for charging the battery from the charging device through the interface; generate health information of the user, at least based on the first bio-signal and the second bio-signal; and display the generated health information on the display.

A charging device according to various embodiments may include an RF sensor, a charging circuit, and an interface, wherein, while the charging device is connected to an electronic device, the charging circuit is configured to supply power to the electronic device and receive a driving signal for driving the RF sensor from the electronic device through the interface, the RF sensor is configured to generate an RF signal, in response to the reception of the driving signal, and the RF sensor is configured to measure a user's bio-signal generated by the RF signal and transmit the measured bio-signal to the electronic device through the interface.

According to various embodiments, a non-transitory computer readable recording medium may store instructions configured to, when executed by a processor, cause the processor to: determine whether a user is wearing an electronic device by using at least one sensor included in the electronic device, and measure a first bio-signal of the user by using the at least one sensor while the user is wearing the electronic device; while the electronic device is connected to a charging device including an RF sensor, drive the RF sensor included in the charging device, and measure a second bio-signal of the user, the second bio-signal being generated by an RF signal oscillated from the RF sensor; receive, from the charging device, at least one of the second bio-signal and power for charging a battery included in the electronic device; generate health information of the user, at least based on the first bio-signal and the second bio-signal; and display the generated health information on a display.

According to various embodiments of the disclosure, in order to measure bio-information of a user continuously for 24 hours, the inconvenience of the user having to wear a wearable electronic device at all times can be eliminated.

According to various embodiments of the disclosure, a user can obtain meaningful health information by measuring bio-information continuously for 24 hours.

According to various embodiments of the disclosure, a charging device is used to measure bio-information of a user by using time for charging a wearable electronic device, so that bio-information of a user can be continuously measured even when the user is not wearing the wearable electronic device.

BRIEF DESCRIPTION OF THE DRAWINGS

FIG. 2A illustrates structures of an electronic device according to an embodiment of the disclosure;

FIG. 2B illustrates structures of an electronic device according to an embodiment of the disclosure;

FIG. 3A illustrates a structure of a charging device and a structure in which an electronic device is mounted on the charging device according to an embodiment of the disclosure;

FIG. 3B illustrates a structure of a charging device and a structure in which an electronic device is mounted on the charging device according to an embodiment of the disclosure;

DETAILED DESCRIPTION

Figure 1:
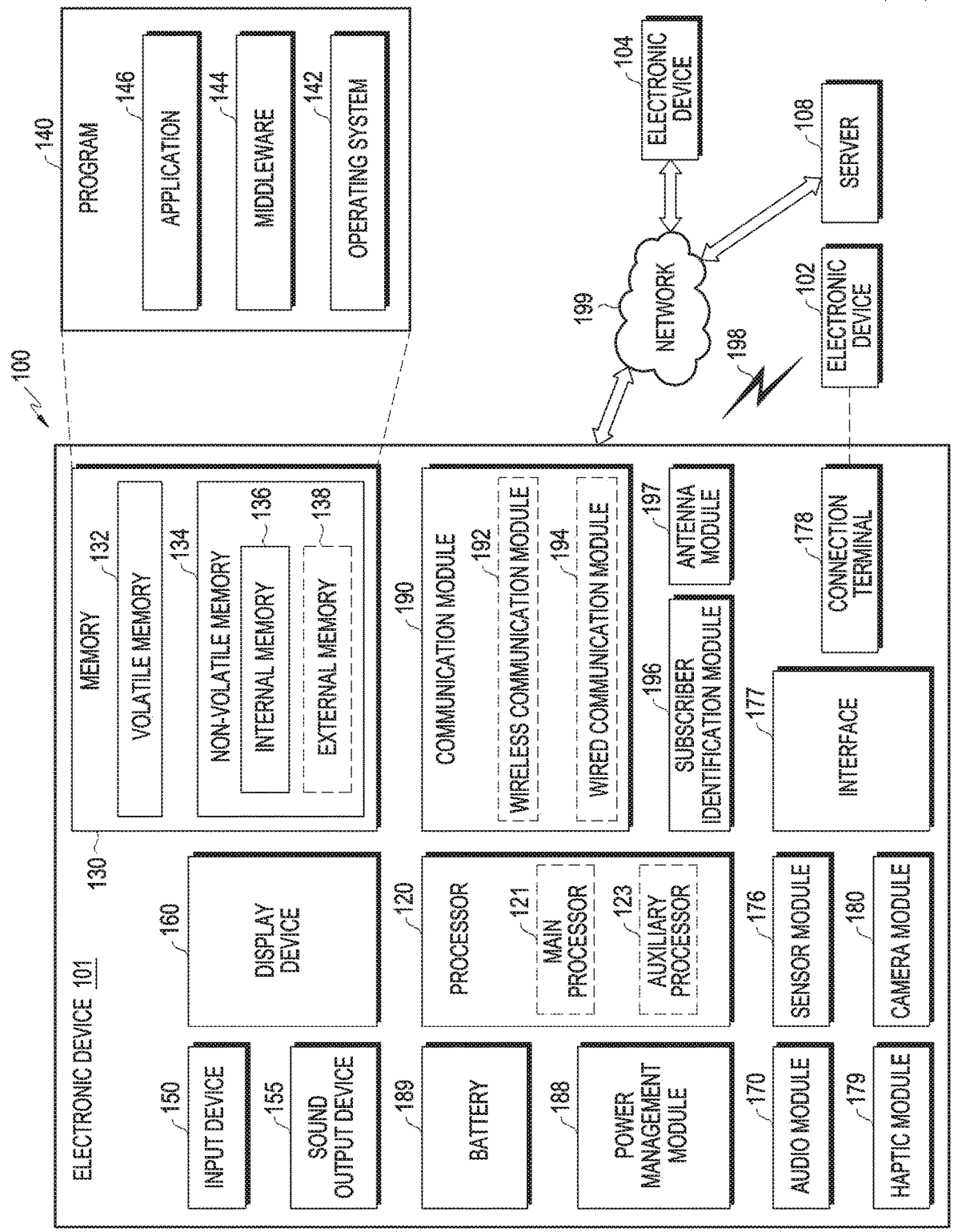
FIG. 1 is a block diagram illustrating an electronic device in a network environment according to an embodiment of the disclosure.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented integrated and implemented as in, for example, the sensor module 176 (e.g., a fingerprint sensor, an iris sensor, or an illuminance sensor) embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing and computation. The processor 120 may load and process a command or data received from another component (e.g., the sensor module 176 or the communication module 190) in volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from the main processor 121. Additionally or alternatively, the auxiliary processor 123 may be adapted to consume less power than the main processor 121, or to be specific to a specified function. Here, the auxiliary processor 123 may be operated separately from or embedded in the main processor 121.

In such a case, the auxiliary processor 123 may control, for example, at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123. The memory 130 may store various data used by at least one component (e.g., the processor 120 or the sensor module 176) of the electronic device 101, for example, software (e.g., the program 140) and input data or output data for a command related thereto. The memory 130 may include the volatile memory 132 or the non-volatile memory 134.

The program 140 is software stored in the memory 130, and may include, for example, an operating system (OS) 142, middleware 144, or an application 146.

The input device 150 is a device configured to receive a command or data to be used by a component (e.g., the processor 120) of the electronic device 101, from the outside (e.g., a user) of the electronic device 101, and may include, for example, a microphone, a mouse, or a keyboard.

The sound output device 155 is a device configured to output sound signals to the outside of the electronic device 101, and may include, for example, a speaker or a receiver. The speaker may be used for general purposes, such as playing multimedia or playing record, and the receiver may be used only for incoming calls. According to an embodiment, the receiver may be implemented as separate from, or as part of the speaker.

The display device 160 is a device configured to visually provide information to a user of the electronic device 101, and may include, for example, a display, a hologram device, or a projector and control circuitry to control a corresponding one of the display, hologram device, and projector. According to an embodiment, the display device 160 may include touch circuitry or a pressure sensor adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or an external electronic device (e.g., an electronic device 102 (e.g., a speaker or a headphone)) wiredly or wirelessly coupled with the electronic device 101.

The sensor module 176 may generate an electrical signal or data value corresponding to an internal operational state (e.g., power or temperature) of the electronic device 101 or an environmental state external to the electronic device 101. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support specified protocols to be used for the electronic device 101 to be coupled with the external electronic device (e.g., the electronic device 102) wiredly or wirelessly. According to an embodiment, the interface 177 may include a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102), for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. The haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 is a module configured to manage power supplied to the electronic device 101, and may be implemented as at least part of, for example, a power management integrated circuit (PMIC).

The battery 189 is a device configured to supply power to at least one component of the electronic device 101, and may include, for example, a primary cell which is not rechargeable, a secondary cell which is rechargeable, or a fuel cell.

The communication module 190 may support establishing a wired communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a wired communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules 190 may be implemented as a single chip or may be implemented as separate chips, respectively.

According to an embodiment, the wireless communication module 192 may identify and authenticate the electronic device 101 in a communication network, using user information stored in the subscriber identification module 196.

The antenna module 197 may include at least one antenna module for transmitting or receiving a signal or power to or from the outside of the electronic device 101. According to an embodiment, the communication module 190 (e.g., the wireless communication module 192) may transmit or receive a signal to or from the external electronic device via an antenna appropriate for a communication scheme.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices. According to an embodiment, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the function requested or an additional function, and transfer an outcome of the performing to the electronic device 101. The electronic device 101 may provide the function or service requested, with or without further processing of the outcome. To that end, a cloud computing, distributed computing, or client-server computing technology may be used, for example.

FIGS. 2A and 2B illustrate structures 200a and 200b of an electronic device 201 according to various embodiments. According to various embodiments, the electronic device 201 (e.g., the electronic device 101 of FIG. 1) may have a wearable form. For example, the electronic device 201 may be a wearable watch, a health band, a smart phone, or the like. Referring to FIG. 2A, the electronic device 201 may include a display 250 (e.g., the display device 160 of FIG. 1), a first electrode sensor 240, and a first optical sensor 242 in a front portion thereof. The front portion of the electronic device 201 may be a portion visible to a user in a state in which the user is wearing the electronic device 201. Referring to FIG. 2B, the electronic device 201 may include a second electrode sensor 241, a second optical sensor 243, and an interface 210 (e.g., the interface 177 of FIG. 1) in a rear portion thereof. The rear portion of the electronic device 201 may be a portion in contact with a part of the body of a user in a state in which the user is wearing the electronic device 201.

According to various embodiments, the electronic device 201 may include a sensor (e.g., the sensor module 176 of FIG. 1), and measure information related to the body of a user by using the sensor while the user is wearing the electronic device 201. Alternatively, the electronic device 201 may measure information on the surrounding environment of the electronic device 201 by using the sensor, regardless of whether the user is wearing the electronic device. In various embodiments, the electronic device 201 may measure heart rate variability (HRV) of a pulse wave signal (photo-plethysmograph: PPG) by using the first optical sensor 242 included in the front portion thereof. For example, when a user comes in contact with the first optical sensor 242 included in the front portion of the electronic device 201 by using a part of the body, such as a finger, the electronic device 101 may measure the heart rate variability. In various embodiments, the electronic device 201 may use the second optical sensor 423 included in the rear portion thereof, so as to measure heart rate variability of a user, based on a pulse wave signal, while the user is wearing the electronic device 201. The electronic device 201 may measure information related to the body of a user, based on data obtained through the first electrode sensor 240 or the second electrode sensor 241. For example, the electronic device 201 may measure body composition, body fat, body impedance analysis (BIA), an electrocardiogram (ECG), or galvanic skin resistance (GSR) by using the first electrode sensor 240 included in the front thereof, or the second electrode sensor 241 included in the rear thereof.

In various embodiments, the electronic device 201 may be connected to a charging device through the interface 210 included in the rear portion thereof. For example, the interface 210 of the electronic device 201 and an interface of the charging device may be connected and in contact with each other. The charging device may have a structure of receiving the electronic device 201 and enabling easy contact of the interface. The electronic device 201 may receive power from the charging device while being connected to the charging device through the interface 210. The electronic device 201 may control a sensor included in the charging device through the interface 210. In various embodiments, the electrode sensor 241 may include the interface 210. For example, the electronic device 201 may come into contact with the body of a user by using the electrode sensor 241, so as to sense information related to the body of the user, and receive, from the charging device, power or data measured by the sensor included in the charging device by using the electrode sensor 241, while the electrode sensor 241 is in contact with the charging device.

The electronic device 201 may display the data measured using the sensor on the display 250 included in the front portion thereof. For example, the electronic device 201 may display a user's heart rate variability measured using the first optical sensor 242 on the display 250. In various embodiments, the electronic device 201 may display information required for controlling the charging device on the display 250 in order to provide the information to a user.

FIGS. 3A and 3B illustrate a structure 300a of a charging device 301 and a structure 300b in which the electronic device 201 is mounted on the charging device 301 according to various embodiments.

Referring to FIG. 3A, the charging device 301 according to various embodiments may have a cradle structure capable of mounting another device thereon. The charging device 301 may be changed in various forms according to a structure of the electronic device 201 to be charged. For example, in correspondence to the structure of the watch-type wearable electronic device 201 of FIG. 2A or 2B, FIG. 3A may illustrate a cradle structure which enables easy mounting of the watch-type wearable electronic device 201. The charging device 301 disclosed in FIG. 3A may have a cradle structure and include an interface 310 which can be connected to the electronic device 201, and an RF sensor 320 which can sense an external object (e.g., the body of a user), based on an RF signal. The interface 310 of the charging device 301 may be connected in physical contact with the interface 210 of the electronic device 201 to be charged. The RF sensor 320 of the charging device 301 may generate an RF signal by a driving signal received from the electronic device 201, and receive an RF signal returned by an oscillated RF signal, so as to measure information related to the body of a user. For example, the RF sensor 320 may measure whether the user moves.

Referring to FIG. 3B, a structure in which the watch-type electronic device 201 is mounted on the charging device 301 having a cradle structure is illustrated. In a state where the electronic device 201 is mounted on the charging device, the charging device 301 may supply power to the electronic device 201. While the electronic device 201 is connected to the charging device 301, the electronic device 201 may control the charging device 301 by transmitting a signal for driving the RF sensor 320 through the interface 210. The charging device 301 according to various embodiments may drive the RF sensor 320 by receiving a control signal for the RF sensor 320 from the electronic device 201, while being connected to the electronic device 201. The charging device 301 may receive a bio-signal generated from a user who has received an RF signal oscillated by the RF sensor 320. For example, the charging device 301 may measure breathing of the user by using the RF sensor 320.

Figure 4:
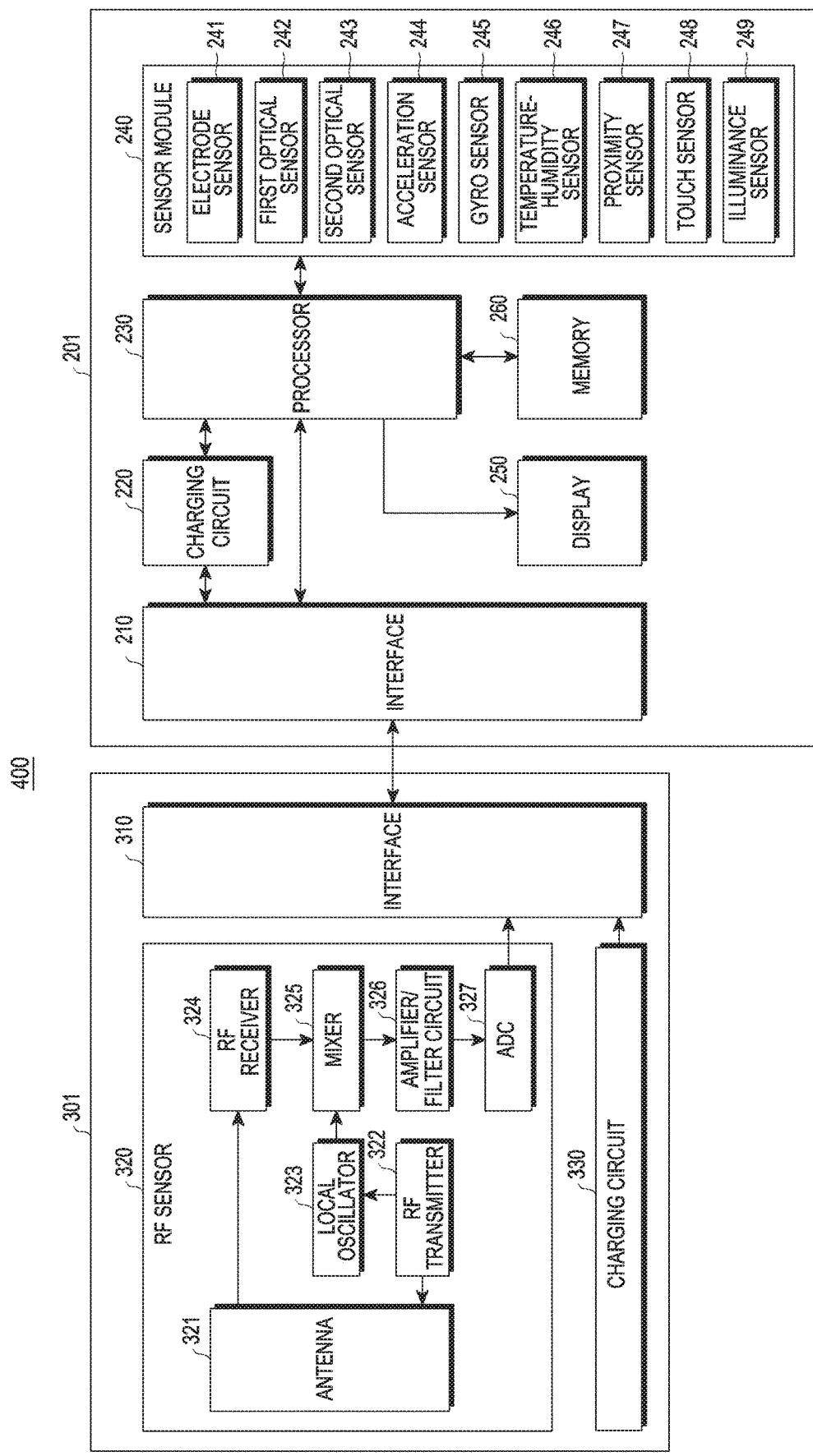
FIG. 4 illustrates a block diagram of an electronic device and a charging device according to an embodiment of the disclosure.

FIG. 4 illustrates a block diagram 400 of the electronic device 201 and the charging device 301 according to various embodiments. The electronic device 201 according to various embodiments may include the interface 210 (e.g., the interface 177 of FIG. 1), a charging circuit 220 (e.g., the power management module 188 of FIG. 1), a processor 230 (e.g., the processor 120 of FIG. 1), a sensor module 240 (e.g., the sensor module 176 of FIG. 1), the display 250 (e.g., the display device 160 of FIG. 1), and a memory 260 (e.g., the memory 130 of FIG. 1). The charging device 301 according to various embodiments may include the interface 310, the RF sensor 320, and a charging circuit 330. According to various embodiments, the interface 210 of the electronic device 201 may be connected in physical contact with the interface 310 of the charging device 301. The electronic device 201 may be connected to the charging device 301 to transmit or receive power and data to or from the charging device through the respective interfaces 210 and 310. The interfaces 210 and 320 may be interfaces which can provide power or transmit data. For example, the electronic device 201 may receive power from the charging device 301 through the interface 210. The electronic device 201 may transmit an RF driving signal through the interface 210 to drive the RF sensor 320 of the charging device 301. The electronic device 201 may receive, through the interface 210, sensing data measured by the RF sensor 320 of the charging device 301. The charging device 301 may receive an RF sensor driving signal and a charging request signal through the interface 310.

According to various embodiments, the charging circuit 220 of the electronic device 201 may charge a battery (e.g., the battery 189 of FIG. 1) in the electronic device 201 by using power received from the charging device 301. The electronic device 201 may request power from the charging device 301, based on the remaining battery power in the electronic device 201.

According to various embodiments, the processor 230 of the electronic device 201 may control other components in the electronic device 201. In various embodiments, the processor 230 may control to transmit or receive power or data to or from the charging device 301 through the interface 210. The processor 230 may control at least one sensor included in the sensor module 240. The processor 230 may drive the sensor module 240 for measuring a bio-signal of a user, based at least in part on a wearing state of the user and a mounting state of the electronic device, and transmit a control signal for driving the RF sensor 320 of the charging device 301. In various embodiments, the processor 230 may analyze the obtained bio-signal of the user to obtain a heart rate, detection of wearing, an exercise time, a sleeping time, a sleep state, a stress level, temperature information, or moisture information of the user.

According to various embodiments, the sensor module 240 of the electronic device 201 may include at least one sensor. In various embodiments, the sensor module 240 may include the electrode sensor 241, the first optical sensor 242, the second optical sensor 243, an acceleration sensor 244, a gyro sensor 245, a temperature-humidity sensor 246, a proximity sensor 247, a touch sensor 248, and an illuminance sensor 249. The electrode sensor 241 may be a sensor using an electrode. In various embodiments, the electrode sensor 241 may be included in a front portion or a rear portion of the electronic device 201, and may come into contact with the body of a user to sense information related to the body of the user. For example, the electrode sensor 241 may measure a body composition value of the user. The electronic device 201 may obtain various pieces of information by using at least one sensor of the sensor module 240. For example, the electronic device 201 may measure information related to the user's body, such as the number of steps, an exercise type, an exercise state, a skin temperature, ambient light, illuminance, heart rate, and body fat, by using at least one of the acceleration sensor 244, the gyro sensor 245, the temperature-humidity sensor 246, the proximity sensor 247, the touch sensor 248, the electrode sensor 241, and the optical sensors 242 and 243. According to various embodiments, the first optical sensor 242 or the second optical sensor 243 may measure pulse waves by using one or more emitters/detectors (e.g., a light emitting diode (LED)/a photo diode (PD)). The processor 230 may analyze a heart rate from pulse wave signals measured by the optical sensors 242 and 243, identify heart rate variability, and determine a stress level, based on the heart rate variability. The processor 230 may determine a stress level by comparing and analyzing the user's heart rate variability analyzed based on information on the stress level according to the determined heart rate variability. In various embodiments, the electronic device 201 may measure a user's sleep state by using the optical sensors 242 and 243. The electronic device 201 may include the first optical sensor 242 in the front portion thereof and the second optical sensor 243 in the rear portion thereof, so as to measure the user's body or to measure the surrounding environment of the electronic device. For example, the optical sensors 242 and 243 may measure breathing in the user's sleep state. In addition, a movement state of the electronic device 201 may be measured by using the acceleration sensor 244. The processor 230 may analyze the movement state of the electronic device 201 to determine whether the user moves, and determine an activity state or sleep state of the user, based on the determined movement of the user. For example, based on sensing data obtained through the acceleration sensor 244, the processor 230 may obtain information such as a sleeping time and a sleep stage of the user. In various embodiments, blue light and the intensity of ambient light around the electronic device 201 may be measured by using the first optical sensor 242 included in the front portion of the electronic device 201. In various embodiments, through a touch IC connected to the electrode sensor 241, functions such as menu selection, menu movement, notification deletion, and telephone connection may be executed by using the electrode sensor 241 included in the front or the rear of the electronic device 201. The processor 230 of the electronic device 201 may control the sensor module 240 and analyze data sensed by the sensor module 240. The processor 230 may store, in the memory 260, health information generated by calculating or analyzing the sensed data.

According to various embodiments, the display 250 of the electronic device 201 may display health information of a user, a notice, and the like measured by the electronic device 201. Alternatively, the display 250 may display data received from the charging device 301.

According to various embodiments, the memory 260 of the electronic device 201 may store user information of the electronic device 201, information obtained by the sensor module 240 of the electronic device 201, health information of a user, which is generated by analyzing or calculating sensed data, and the like.

According to various embodiments, the interface 310 of the charging device 301 may operate in connection with the interface 210 of the electronic device 201. For example, the interface 310 may transmit power to the electronic device 201 or receive a control signal related to the transmission of power, or an RF driving signal.

According to various embodiments, the RF sensor 320 of the charging device 301 may include an antenna 321, an RF transmitter 322, a local oscillator 323, an RF receiver 324, a mixer 325, an amplifier/filter circuit 326, and an analog digital converter (ADC) 327. The RF sensor 320 may be operated by receiving an RF driving signal from the electronic device 201 while the charging device 301 is connected to the electronic device 201 through the interface 310. The RF sensor 320 may oscillate an RF signal and receive a signal (e.g., a user's bio-signal) generated by the oscillated RF signal. The local oscillator 323 may oscillate an RF signal in response to the driving signal received from the electronic device 201. The RF transmitter 322 may radiate an RF signal through the antenna 321. The RF receiver 324 may receive, through the antenna 321, a reflected signal obtained after the radiated RF signal is reflected by an external object (e.g., a user's body). The mixer 325 may mix a signal transmitted by the RF transmitter 322 and a signal from the RF receiver 324. The amplifier/filter circuit 326 may obtain a reception signal from the signal mixed by the mixer 325. The ADC 327 may convert the reception signal into a digital signal. The reception signal having been converted into the digital signal may be transmitted to the electronic device 201 through the interface 310. Each configuration in the RF sensor 320 of the charging device 301 may be controlled by receiving a driving signal or a control signal from the processor 230 of the electronic device 201 through the interface 310.

In various embodiments, the electronic device 201 may include the RF sensor 320 of the charging device 301, although not shown in the drawings. The electronic device 201 may measure a bio-signal of a user by using an RF sensor (not shown) included in the electronic device 201. In various embodiments, when the electronic device 201 is mounted on the charging device 301 for charging, the electronic device 201 may measure a bio-signal of a user by using the RF sensor even in a state where the user is not wearing the electronic device. For example, while the electronic device 201 is mounted on the charging device 301, the electronic device 201 may drive the RF sensor included in the electronic device 201 to measure inhalation or exhalation of the user.

According to various embodiments, the charging circuit 330 of the charging device 301 may supply power to the electronic device 201 through the interface 310.

Figure 5:
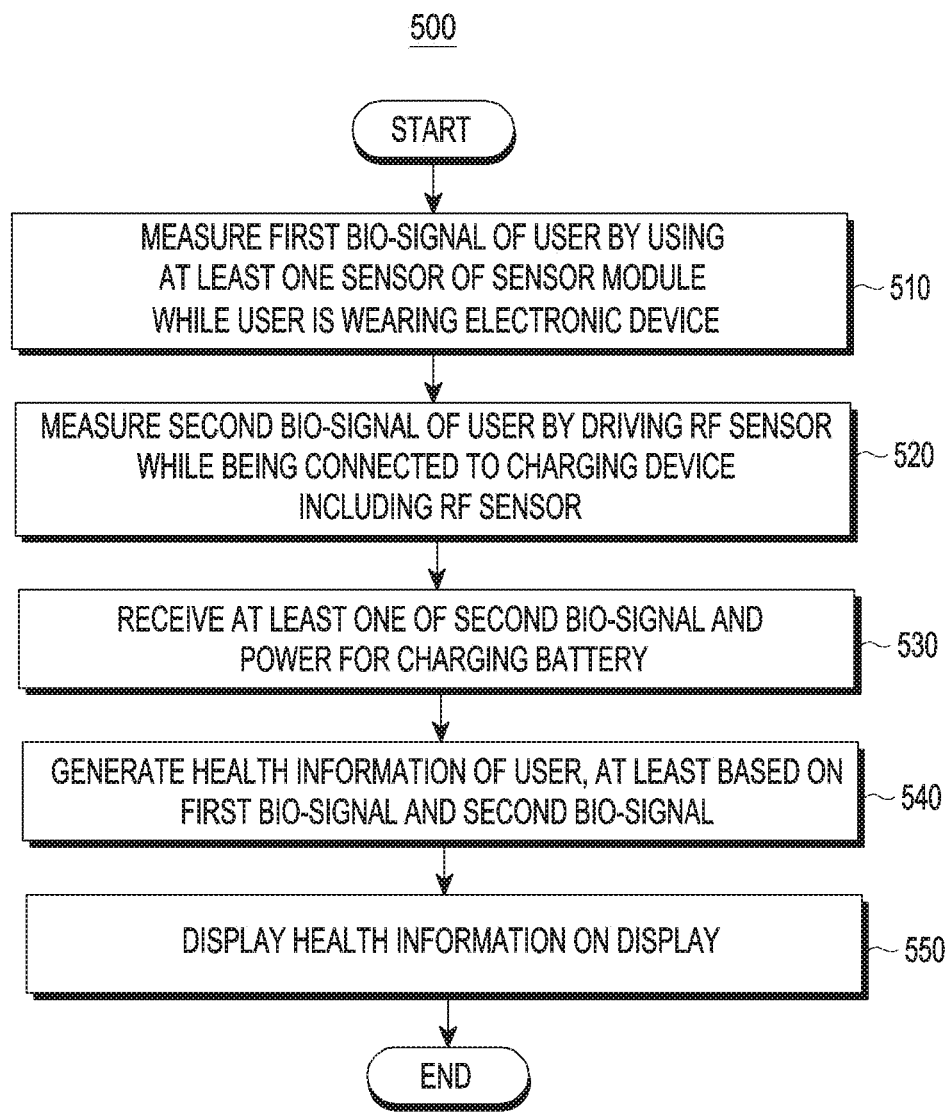
FIG. 5 is a flowchart illustrating an operation method for an electronic device according to an embodiment of the disclosure.

FIG. 5 is a flowchart 500 illustrating an operation method for an electronic device (e.g., the electronic device 201 of FIG. 4) according to various embodiments. According to various embodiments, the electronic device 201 including at least one sensor 240 may measure a bio-signal of a user by using the at least one sensor 240 of the electronic device 201 and a charging device (e.g., the charging device 301 of FIG. 4) including an RF sensor (e.g., the RF sensor 320 of FIG. 4).

In operation 510, the electronic device 201 according to various embodiments may determine whether a user is wearing the electronic device 201 by using at least one sensor of the sensor module 240, and while the user is wearing the electronic device 201, the electronic device 201 may measure a first bio-signal of the user by using the at least one sensor of the sensor module 240. For example, when the user is wearing the wearable electronic device 201 on his/her wrist, heart rate variability, peripheral oxygen saturation (Sp02), and the like of a pulse wave signal of the user may be measured by using the optical sensor 243 included in the rear portion of the electronic device 201. In various embodiments, the electronic device 201 may determine whether the body of the user is in contact with at least one sensor of the sensor module 240, and measure the first bio-signal of the user by using a sensor in contact with the user, while the body of the user is in contact with the electronic device 201. For example, when the user is not wearing the electronic device 201 and comes in contact with the optical sensor 242 included in the front portion of the electronic device 201 by using his/her finger, the electronic device 201 may measure heart rate variability of the user by using the optical sensor 242. Alternatively, the electronic device 201 may measure a skin temperature of the user by using the temperature-humidity sensor 246, or measure the temperature of the surrounding environment of the electronic device 201.

In operation 520, while the electronic device 201 is connected to the charging device 301 including the RF sensor 320, the electronic device 201 may drive the RF sensor 320 included in the charging device 301, so as to measure a second bio-signal of the user, the second bio-signal being generated by an RF signal oscillated from the RF sensor 320. According to an embodiment, the electronic device 201 may transmit a signal for driving the RF sensor 320 included in the charging device 301, and the RF sensor 320 of the charging device 301 may oscillate an RF signal in response to the signal received from the electronic device 201, and receive a signal generated by reflection of the RF signal by the body of the user, so as to measure the second bio-signal of the user. According to an embodiment, the charging device 301 does not include a separate processor, and can be directly controlled by the electronic device 201. For example, the electronic device 201 may transmit a driving signal for driving the RF sensor 320 of the charging device 301, through the interface 310 of the charging device 301. The interface 310 of the charging device 301 may receive a driving signal for the RF sensor 320 from the electronic device 201 and transmit the signal to the RF sensor 320, so as to generate an RF signal and receive a signal generated corresponding thereto. In various embodiments, the charging device 301 may optionally include a processor. According to an embodiment, in response to the signal received from the electronic device 201, the processor (not shown) included in the charging device 301 may drive the RF sensor 320 to measure a bio-signal of the user.

In operation 530, the electronic device 201 may receive, from the charging device 301, at least one of the second bio-signal and power for charging a battery (e.g., the battery 189 of FIG. 1). While the electronic device 201 is connected to the charging device 301, the electronic device 201 may receive power from the charging device 301 to charge the battery (e.g., the battery 189 of FIG. 1). When the electronic device 201 is connected to the charging device 301, the electronic device 201 may request power for charging the battery (e.g., the battery 189 of FIG. 1) of the electronic device 201 from the charging device 301 through a charging circuit. The electronic device 201 may receive, through the interface 210, the power transmitted by the charging device 301, in response to the request for charging. While the electronic device 201 is connected to the charging device 301, the electronic device 201 may receive the second bio-signal sensed by the RF sensor 320 of the charging device 301 from the charging device 301.

In operation 540, the electronic device 201 may generate health information of the user, at least based on the first bio-signal and the second bio-signal. The electronic device 201 may generate health information of the user in an active state, based on the first bio-signal measured while the user is wearing the electronic device 201. The electronic device may generate health information of the user in a sleep state, based on the second bio-signal measured while the user is not wearing the electronic device 201 and the electronic device is mounted on the charging device 301. The electronic device 201 may continuously measure a bio-signal of the user by using the charging device 301 even in a state where the user is not wearing the electronic device. For example, the user may receive the health information of the user by wearing the electronic device 201 while doing an activity during the day, and mounting the electronic device 201 on the charging device 301 while sleeping at night.

In operation 550, the electronic device 201 may display the generated health information on the display 250. The electronic device 201 may visualize the health information to provide the health information to the user. According to various embodiments, the electronic device 201 may transmit the health information to an external electronic device (e.g., the electronic device 102, the electronic device 104, or the server 108 of FIG. 1) by using a communication module (e.g., the communication module 190 of FIG. 1).

Figure 6:
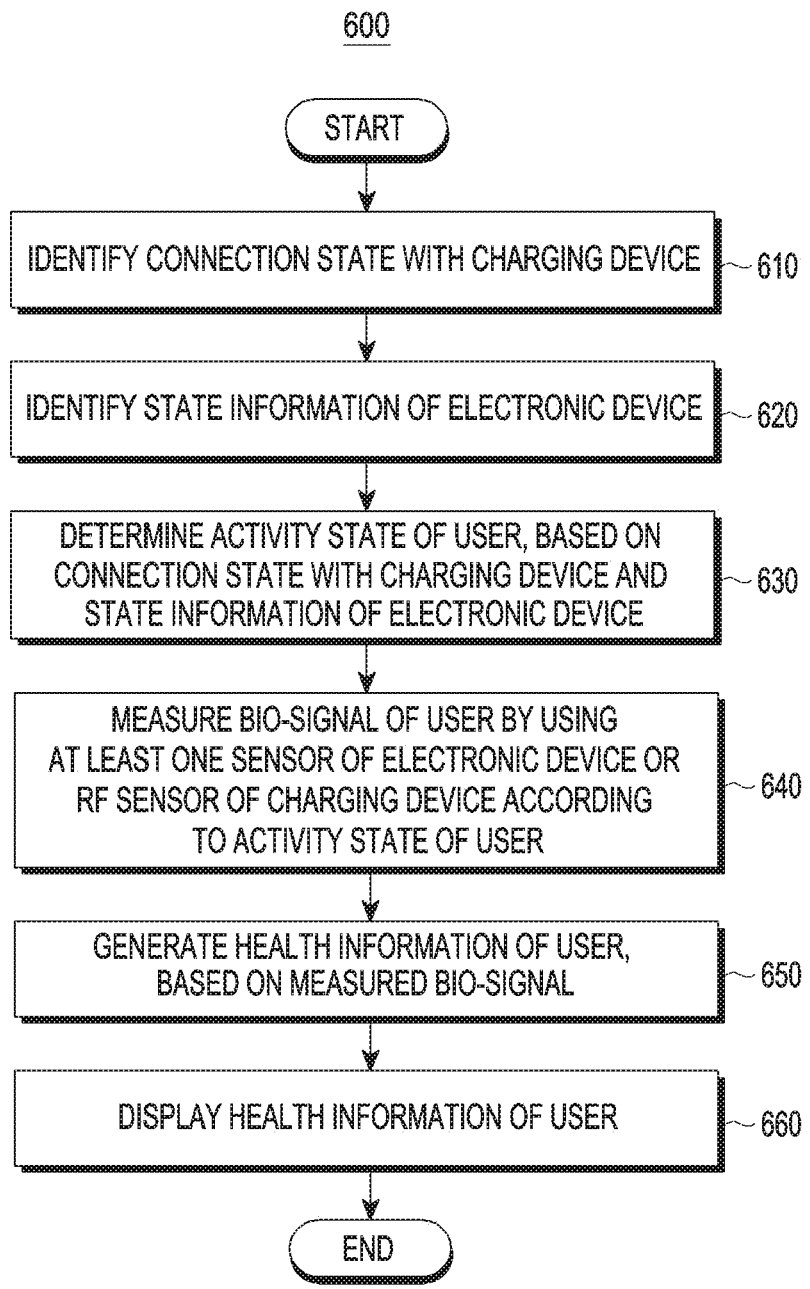
FIG. 6 is a flowchart illustrating a method for measuring, by an electronic device, a bio-signal of a user according to an activity state of the user according to an embodiment of the disclosure.

FIG. 6 is a flowchart 600 illustrating a method for measuring, by an electronic device, a bio-signal of a user according to an activity state of the user according to various embodiments.

In operation 610, an electronic device (e.g., the electronic device 201 of FIG. 4) according to various embodiments may identify a connection state with a charging device (e.g., the charging device 301 of FIG. 4). The electronic device 201 may be connected to the charging device 301 through an interface (e.g., the interface 210 of FIG. 4), and may identify whether the electronic device is connected to the charging device 301 through the interface 210.

In operation 620, the electronic device 201 may identify state information of the electronic device 201. The electronic device 201 may identify whether the electronic device 201 is in a moving state, and location information by using at least one sensor (e.g., the acceleration sensor 244 or the gyro sensor 245) of a sensor module (e.g., the sensor module 240 of FIG. 4) included in the electronic device 201. The electronic device 201 may identify state information related to a battery (e.g., the battery 189 of FIG. 1). For example, the electronic device 201 may identify the remaining battery power and determine whether the electronic device 201 requires charging, based on the remaining battery power.

In operation 630, the electronic device 201 may determine an activity state of a user, based on a connection state with the charging device 301 and state information of the electronic device 201. When the electronic device 201 is not connected to the charging device 301 and the electronic device 201 is in a moving state, the electronic device 201 may determine that the user is in an active state while wearing the electronic device. When the electronic device 201 is not connected to the charging device 301, but the electronic device 201 is in a stopped state, the electronic device 201 may determine that the user is active and in a sitting state or lying down and sleeping, while wearing the electronic device. If the electronic device 201 is connected to the charging device 301, the user is not wearing the electronic device 201, and thus the electronic device 201 may determine the activity state of the user as a sleep state.

In operation 640, the electronic device 201 may measure a bio-signal of the user by using at least one sensor (e.g., the sensor module 240 of FIG. 4) of the electronic device 201 or an RF sensor (e.g., the RF sensor 320 of FIG. 4) of the charging device 301 according to the activity state of the user. When the electronic device 201 determines that the user is in an active state while wearing the electronic device 201, the electronic device 201 may obtain information related to the user's body by driving at least one sensor (e.g., the sensor module 240 of FIG. 4) included in the electronic device 201. When the electronic device 201 is connected to the charging device 301 and determines that the user is in a sleep state, the electronic device 201 may obtain information related to the user's body by driving the RF sensor 320 of the charging device 301 connected to the electronic device 201 through the interfaces 210 and 310. In various embodiments, when the remaining battery power is less than a predetermined threshold value, the electronic device 201 may control not to drive the RF sensor 320 of the charging device 301 even when the electronic device 201 is connected to the charging device 301.

In operation 650, the electronic device 201 may generate health information of the user, based on the measured bio-signal. While the user is sleeping, the electronic device 201 may analyze sensing data obtained by measuring the user's breathing through the RF sensor 320 of the charging device 301, so as to divide a state of sleep. For example, the state of sleep may be divided into a rapid eye movement (REM) sleep state, an awake state, a light sleep state, and a deep sleep state. The electronic device 201 may analyze a change in the state of sleep while the user is sleeping, determine a health level of the user, and generate health information of the user.

In operation 660, the electronic device 201 may display the health information of the user on the display 250. For example, the electronic device may visualize and display information on a sleeping time, a sleeping pattern, or a sleep quality.

Figure 7A:
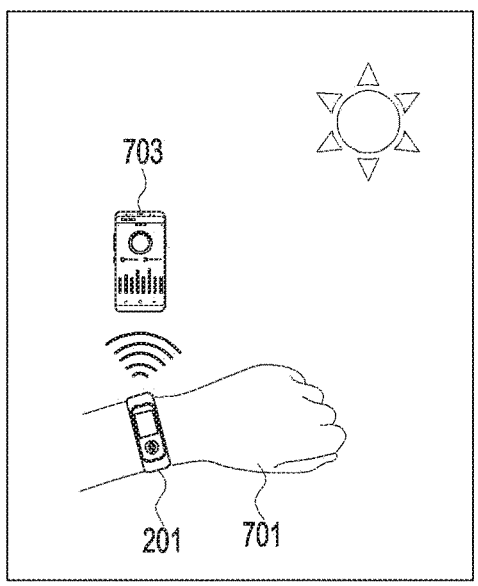
FIG. 7A is a conceptual diagram illustrating a method for continuously measuring a bio-signal of a user by an electronic device according to an embodiment of the disclosure.
Figure 7B:
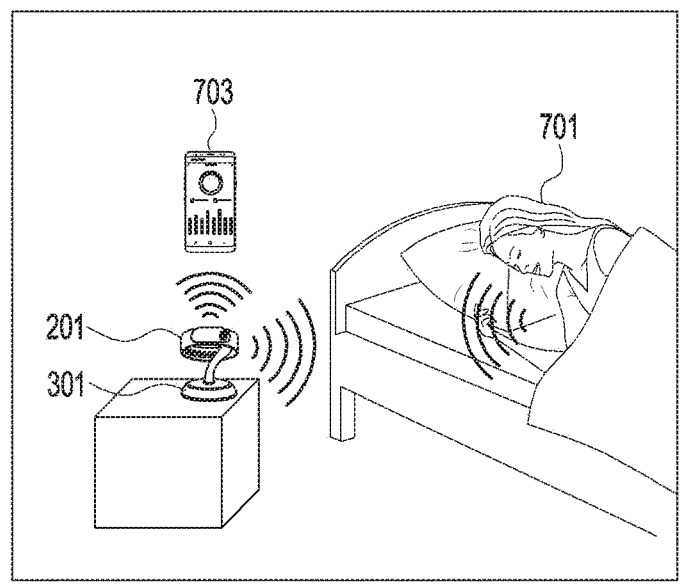
FIG. 7B is a conceptual diagram illustrating a method for continuously measuring a bio-signal of a user by an electronic device according to an embodiment of the disclosure.

FIGS. 7A and 7B are conceptual diagrams 700a and 700b illustrating a method for continuously measuring a bio-signal of a user by an electronic device according to various embodiments.

The electronic device 201 (e.g., the electronic device 201 of FIG. 4) according to various embodiments may be worn on a wrist of a user 701 in a wearable form to operate. For example, referring to FIG. 7A, the electronic device 201 may be worn on a wrist of the user to measure an activity state of the user. The electronic device 201 may obtain information related to the body of the user by using at least one sensor (e.g., the sensor module 240 of FIG. 4). The electronic device 201 may generate health information of the user by analyzing the information related to the measured user's body, and transmit the generated health information to an external electronic device 703 (e.g., the electronic device 102 or 104 of FIG. 1) connected to the electronic device 201. In various embodiments, the external electronic device 703 may provide a function linked with the electronic device 201. For example, the external electronic device 703 may be a mobile device, and the electronic device 201 may be a wearable device which is linked with the mobile device to provide functions such as a phone call, message reception, and alarm.

The electronic device 201 according to various embodiments may be operated by being mounted on the charging device 301 (e.g., the charging device 301 of FIG. 4) while not being worn. For example, referring to FIG. 7B, the electronic device may be mounted on and connected to the charging device 301 to measure a sleep state of the user during charging. The electronic device 201 may control the connected charging device 301 so as to drive the RF sensor 320 included in the charging device 301 and measure the breathing of the user 701 who is asleep. The electronic device 201 may receive, from the charging device 301, data obtained by measuring the breathing of the user 701 who is asleep and analyze the data to generate health information on a sleep state of the user. The electronic device 201 may transmit the health information to the external electronic device 703 connected to the electronic device 201. The electronic device 201 may obtain a bio-signal obtained during the user's activity time and a bio-signal obtained during the user's sleeping time, and thus analyze all continuous bio-signals of the user generated in one day.

Figure 8:
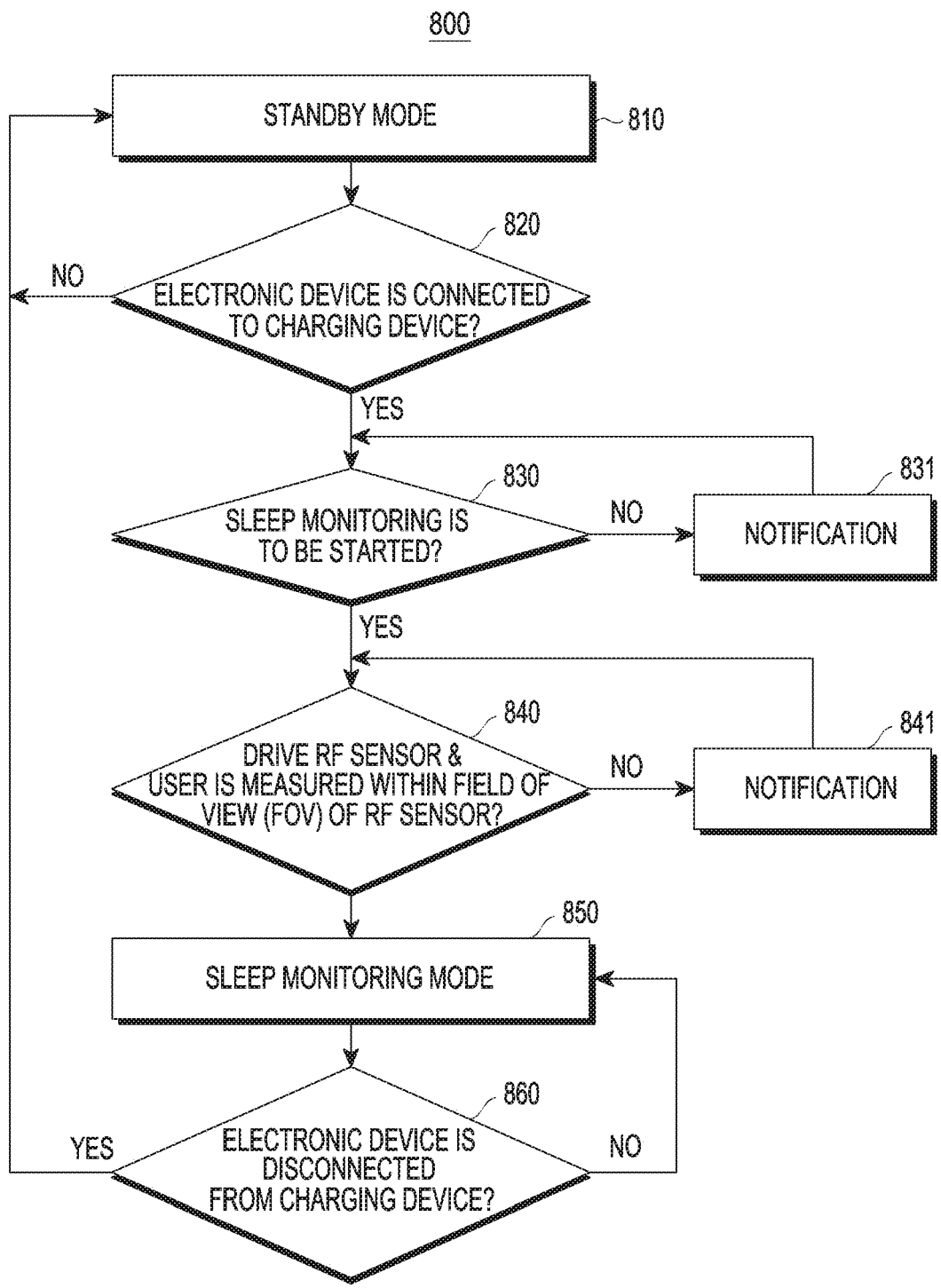
FIG. 8 is a flowchart illustrating a method for controlling a charging device by an electronic device according to an embodiment of the disclosure.

FIG. 8 is a flowchart 800 illustrating a method for controlling a charging device by an electronic device according to various embodiments.

In operation 810, the electronic device 201 according to various embodiments may be in a standby mode. In various embodiments, the electronic device 201 may perform a predetermined operation according to various events occurring in the standby mode.

In operation 820, the electronic device 201 may identify whether the electronic device 201 is connected to the charging device 301. The electronic device 201 may determine whether the interface 210 is in contact with the interface 310 of the charging device 301, and may determine that the electronic device is connected to the charging device 301 when the electronic device is in physical contact with the charging device 301. The electronic device 201 may generate an event signal corresponding to a connection with the charging device 301.

In operation 830, the electronic device 201 may identify whether to start sleep monitoring. In various embodiments, the electronic device 201 may be configured to automatically execute the sleep monitoring in response to the event signal generated corresponding to the connection with the charging device 301. Alternatively, the electronic device 201 may display a connection notification on a display in response to the connection with the charging device 301, and receive an input for starting of the sleep monitoring from a user. In various embodiments, the electronic device 201 may be configured to measure illuminance through at least one sensor (e.g., the sensor module 240 of FIG. 4) after the electronic device 201 is connected to the charging device 301, and to start the sleep monitoring when it is determined that the measured illuminance satisfies a predetermined sleep condition.

In operation 831, when the electronic device 201 determines not to start sleep monitoring, the electronic device 201 may provide a notification through the display. In various embodiments, when the electronic device 201 determines that the predetermined sleep condition is not satisfied within a predetermined time based on the predetermined sleep condition, the electronic device 201 may determine not to start the sleep monitoring. The electronic device 201 may provide a notification including information indicating that the sleep monitoring is not to be started since the sleep condition is not satisfied. After the notification, the electronic device 201 may determine the sleep condition again in operation 830.

In operation 840, the electronic device 201 may drive an RF sensor to determine whether the user is detected within a field of view (FOV) of the RF sensor. In various embodiments, the electronic device 201 may measure information related to the body of the user by using the RF sensor 320 included in the charging device 301 while being connected to the charging device 301. In order to measure the body of the user by using the RF sensor 320, the electronic device 201 may identify whether the user is measured within a sensing range of the RF sensor 320. The electronic device 201 may drive the RF sensor 320 and determine that there is no object to be measured, when the user is not measured within the sensing range of the RF sensor 320 within a predetermined time.

In operation 841, the electronic device 201 may drive the RF sensor 320 included in the charging device 301 and provide a notification through the display 250 when the user is not measured within the sensing range of the RF sensor 320 within the predetermined time. For example, the electronic device 201 may display, on the display 250, an indication that the object to be measured does not exist by using a predetermined emoticon.

In operation 850, the electronic device 201 may start a sleep monitoring mode. In the sleep monitoring mode, the electronic device 201 may measure surrounding environment information and information related to the body of the user by using at least one sensor (e.g., the sensor module 240 of FIG. 4) included in the electronic device 201, and measure information related to the body of the user by using the RF sensor 320 included in the charging device 301. For example, while the user is sleeping, the electronic device 201 may measure a sleeping environment by using the temperature-humidity sensor 246 included in the electronic device 201, and measure sleep breathing through the RF sensor 320 included in the charging device 301.

In operation 860, the electronic device 201 may determine whether the electronic device 201 is disconnected from the charging device 301. In various embodiments, when the electronic device 201 is not in contact with the charging device 301, the electronic device 201 may determine that the electronic device 201 is disconnected from the charging device. When the electronic device 201 is disconnected from the charging device 301, the electronic device 201 may return to the standby mode again. While a connection between the electronic device 201 and the charging device 301 is maintained, the electronic device 201 may perform the sleep monitoring mode.

Figure 9:
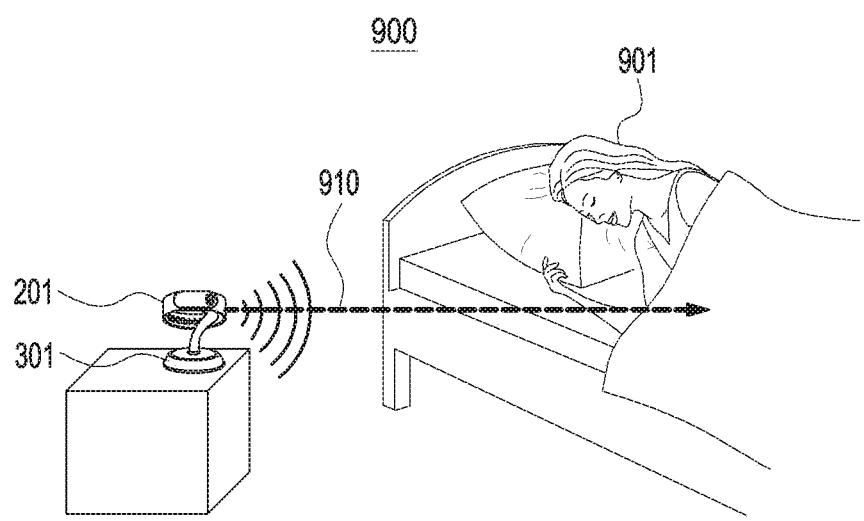
FIG. 9 is an example of a situation in which an electronic device controls an LED target indicator of a charging device according to an embodiment of the disclosure.

FIG. 9 is an example of a situation 900 in which an electronic device controls an LED pointer of a charging device according to various embodiments.

In various embodiments, the electronic device 201 may measure information related to the body of a user through the RF sensor 320 of the charging device 301 while being connected to the charging device 301. The charging device 301 may include an LED pointer, and the electronic device 201 may identify a sensing range of the RF sensor 320 by using the LED pointer of the charging device 301. The charging device 301 may display an indication line 910 indicating the sensing range of the RF sensor 320 of the charging device 301, in response to receiving a driving signal of the LED pointer from the electronic device 201. The electronic device 201 may display the indication line 910 to enable easy identification of whether a location of a user 901 to be measured is included within the sensing range of the RF sensor 320 by using the RF sensor 320. The user 901 may adjust a location or angle of the charging device 301 with reference to the displayed indication line. When a bio-signal of the user 901 is not measured, the electronic device 201 may provide, to the user 901, information for inducing the user 901 to change a location or orientation of the charging device 301. For example, the electronic device 201 may display, on the display 250, as an alarm, that the user 901 is not measured within the sensing range of the RF sensor 320.

Figure 10A:
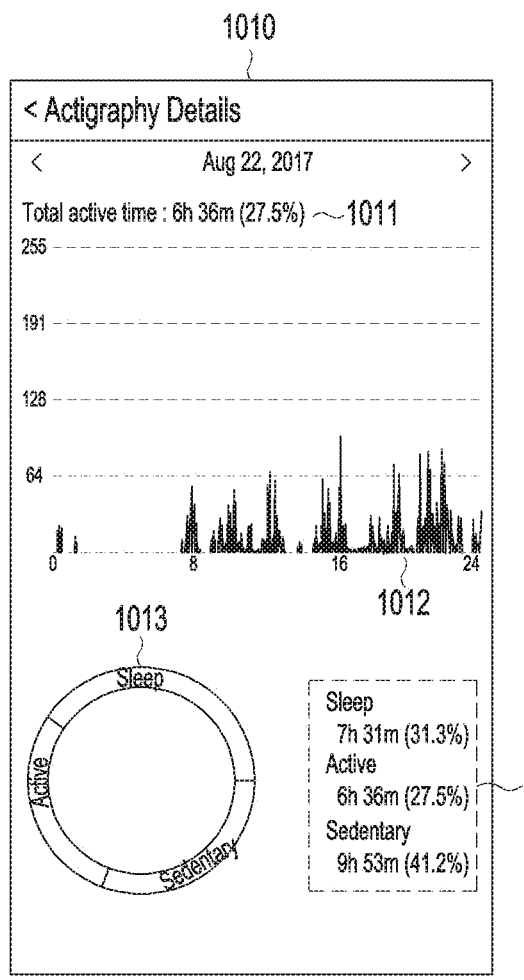
FIG. 10A is an example of displaying health information generated by using a user's bio-signal measured by an electronic device according to an embodiment of the disclosure.
Figure 10B:
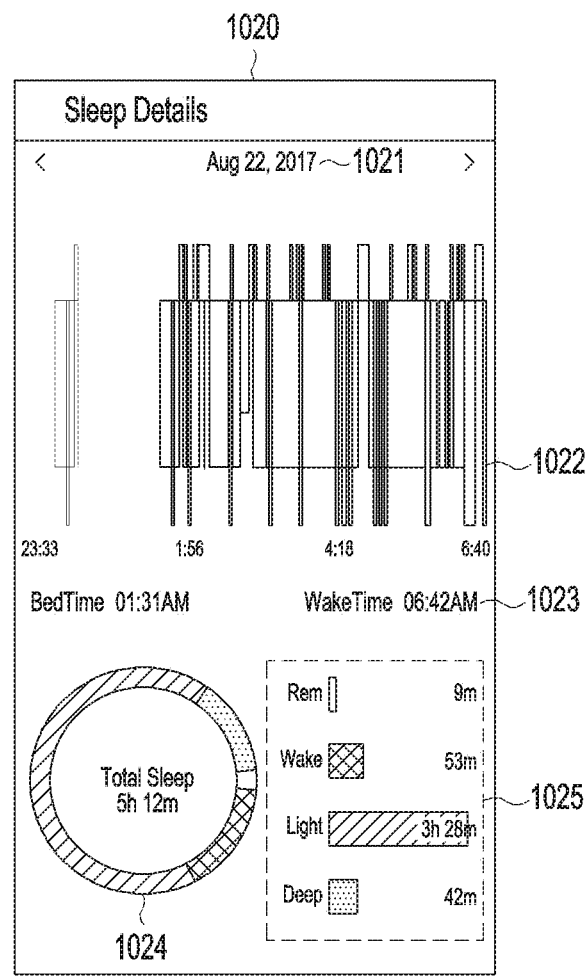
FIG. 10B is an example of displaying health information generated by using a user's bio-signal measured by an electronic device according to an embodiment of the disclosure.

FIGS. 10A and 10B are examples 1000*a* and 1000*b* of displaying health information generated by using a user's bio-signal measured by an electronic device according to various embodiments.

The electronic device 201 according to various embodiments may continuously measure a bio-signal of a user by using at least one sensor (e.g., the sensor module 240 of FIG. 4) included in the electronic device 201 and the RF sensor 320 included in the charging device 301. The electronic device 201 may analyze the obtained bio-signal of the user to generate health information of the user. The electronic device 201 may transmit the health information of the user to an external electronic device (e.g., the electronic device 102 or 104 of FIG. 1) which can be connected with the electronic device 201 to provide a linked function. The external electronic device may include, for example, a mobile device. Referring to FIGS. 10A and 10B, an example in which the mobile device displays the user's health information received from the electronic device 201 is illustrated. In various embodiments, the mobile device may receive health information of 24 hours/7 days from the electronic device 201 by using wireless communication (e.g., Wi-Fi or Bluetooth). The mobile device may provide, to the user, a daily bio-signal and surrounding environment, and an actigraphy.

Referring to FIG. 10A, on a screen 1010, according to various embodiments, the mobile device may display an activity time and an active state of a user for each date. For example, the mobile device may display an activity record of the user on Aug. 22, 2017. The mobile device may display a total activity time 1011 which is 6 hours and 36 minutes, and a graph 1012 indicating an activity level for each time zone. The mobile device may divide the active state of the user into a sleep state, a moving and active state (moving, walking, or running), and a sitting state (sedentary). The mobile device may display the active state according to the activity time of the user by a circle graph 1013 or a table 1014 including numerical values.

Referring to FIG. 10B, on a screen 1020, according to various embodiments, the mobile device may display sleep information in detail. For example, the mobile device may display sleep information 1021 of the user on Aug. 22, 2017. The mobile device may display a sleep type from a sleep start time up to a sleep end time by the graph 1022. The mobile device may display sleep start time information and sleep end information by text 1023. The mobile device may divide the sleep state in detail, and display the sleep state as a REM sleep, an awake state, a light sleep, and a deep sleep. For example, the mobile device may indicate the sleep state by a circle graph 1024 and display the sleep state by a table 1025 including numerical values.

Figure 11:
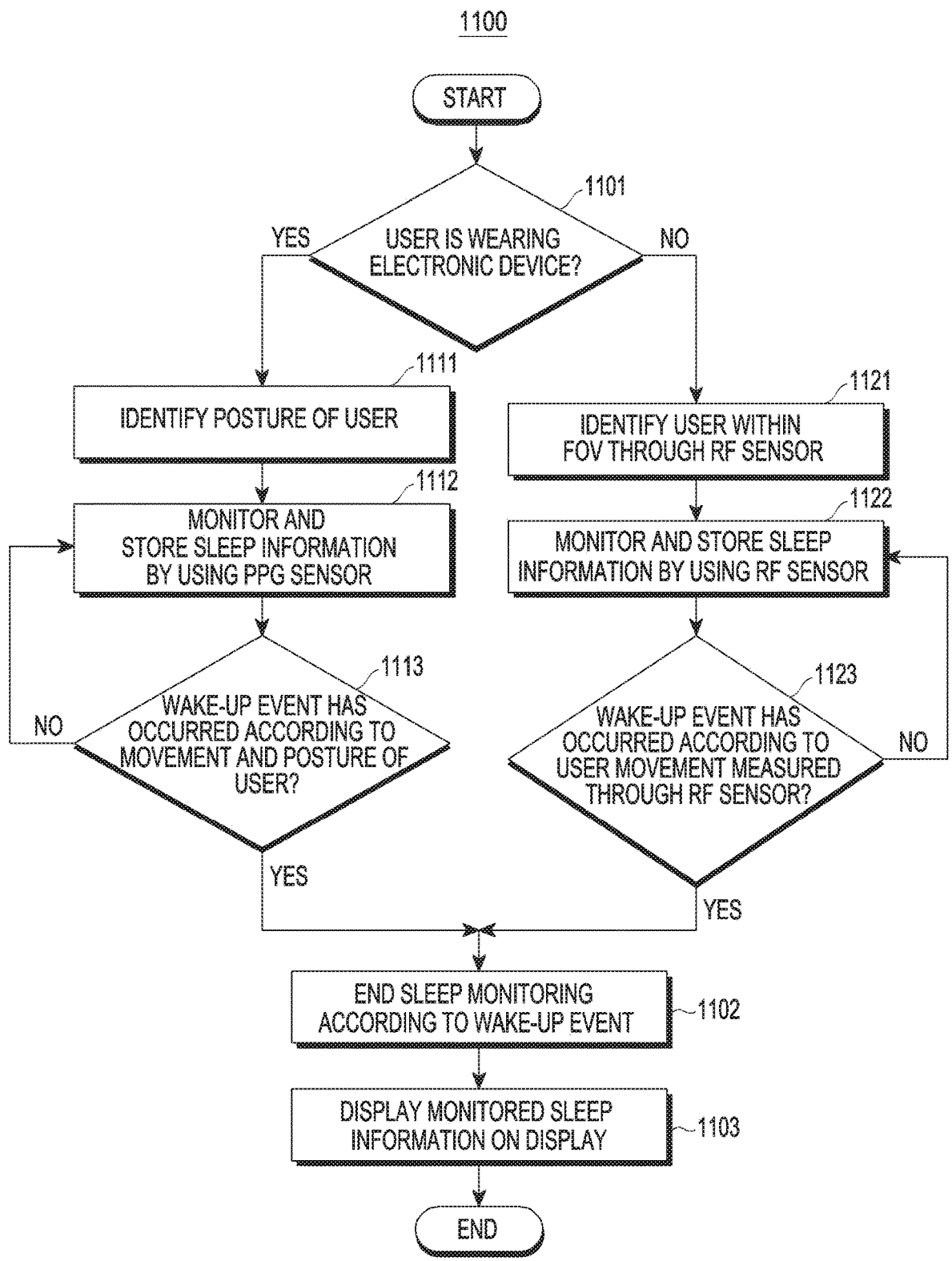
FIG. 11 is a flowchart illustrating a method for monitoring sleep information of a user by using an electronic device and a charging device according to an embodiment of the disclosure.

FIG. 11 is a flowchart 1100 illustrating a method for monitoring sleep information of a user by using an electronic device and a charging device according to various embodiments. In various embodiments, the electronic device 201 may measure a sleep state of a user in a state in which the electronic device is worn by the user or mounted on the charging device 301. For example, when the user sleeps while wearing the electronic device 201, the electronic device 201 may measure information related to the body of the user by using at least one sensor (e.g., the sensor module 240 of FIG. 4) included in the electronic device 201. When the user mounts the electronic device 201 on the charging device 301 and sleeps, the electronic device 201 may measure information related to the body of the user by using a sensor (e.g., the RF sensor 320 of FIG. 4) included in the charging device 301. Referring to FIG. 11, two methods for measuring a sleep state of a user will be described.

In operation 1101, the electronic device 201 according to various embodiments may determine whether the user is wearing the electronic device 201. The electronic device 201 may determine whether the user is in contact with the electronic device through a sensor (e.g., the sensor module 240) included in the electronic device 201, or determine a state in which the electronic device 201 is connected to the charging device 301, so as to identify whether the user is wearing the electronic device 201.

When the user is wearing the electronic device 201, in operation 1111, the electronic device 201 may identify a posture of the user. The electronic device 201 may identify whether the user is moving, a location of the user, and the like by using the acceleration sensor 244, the gyro sensor 245, and the like. For example, the electronic device 201 may determine that the user is in a sleeping posture.

In operation 1112, the electronic device 201 may measure a photoplethysmograph (PPG) of the user by using a PPG sensor, monitor sleep information by using the measured PPG sensor value, and store the sleep information. When the electronic device 201 determines that the user moves within a short time during sleep, and is maintained in a sleeping posture for a predetermined time again, the electronic device 201 may maintain sleep monitoring. In various embodiments, the electronic device 201 may obtain sleep efficiency information during sleep. For example, the electronic device 201 may identify how often the user has twisted and turned within a sleeping time, and may distinguish whether it is a light sleep, a deep sleep, or a REM sleep, based on data measured by the PPG sensor. The electronic device 201 may measure information on how much time is taken from the time of the attempt to sleep to an actual sleep.

In operation 1113, the electronic device 201 may determine whether a wake-up event has occurred according to a movement and posture of the user. In various embodiments, when the electronic device 201 detects a movement of the user, the electronic device 201 may determine that the user has woken up, and determine that the wake-up event has occurred.

In operation 1102, the electronic device 201 may end the sleep monitoring according to the wake-up event.

In operation 1103, the electronic device 201 may display the monitored sleep information on the display 250. In various embodiments, the electronic device 201 may transmit the sleep information of the user to a connected external electronic device (e.g., the electronic device 102 or 104 of FIG. 1) or a server (e.g., the server 108 of FIG. 1). The server having received the sleep information may update the user's sleep information which has been previously stored.

When the user is not wearing the electronic device 201, in operation 1121, the electronic device 201 may identify, through the RF sensor 320 included in the charging device 301, the user within a sensing range of the RF sensor 320. In various embodiments, the electronic device 201 may be mounted on the charging device 301 and may measure information related to the body of the user through the RF sensor 320 included in the charging device 301. When the user is not wearing the electronic device 201, the electronic device 201 may identify whether the user is measured within the sensing range of the RF sensor 320 in order to measure a sleep state of the user through the RF sensor 320 included in the charging device 301.

In operation 1122, the electronic device 201 may monitor sleep information by using the RF sensor 320 of the charging device 301, and store the monitored sleep information. In various embodiments, when the user is identified within the sensing range of the RF sensor 320, the electronic device 201 may start sleep monitoring and measure the breathing or heart rate of the user. For example, the electronic device 201 may measure the breathing, based on a change in the body according to inhalation and exhalation while the user is sleeping, and measure the heart rate, based on subtle movements of the body.

In operation 1123, the electronic device 201 may determine whether a wake-up event has occurred according to the user's movement measured through the RF sensor 320. For example, when the user's movement is detected through the RF sensor 320 of the charging device, the electronic device 201 may determine that the user has woken up, and generate a wake-up event. In operation 1102, the electronic device 201 may end the sleep monitoring according to the wake-up event.

Figure 12:
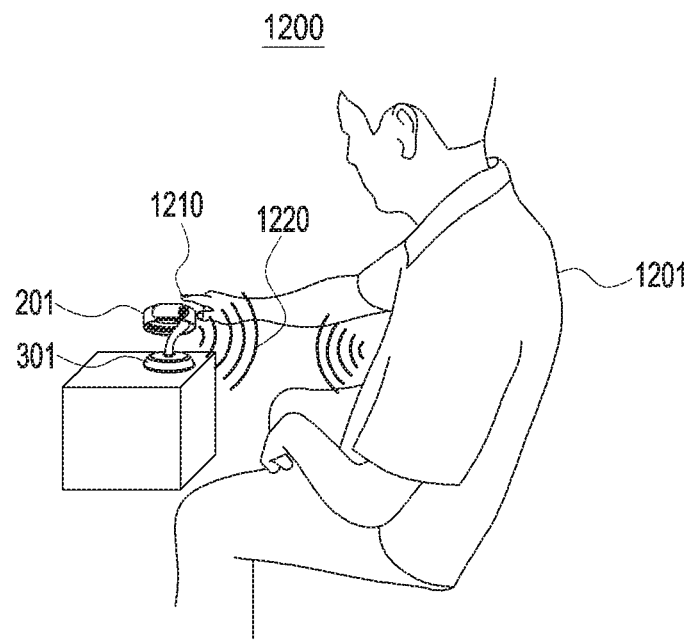
FIG. 12 is a conceptual diagram illustrating a method for measuring a bio-signal of a user by an electronic device and a charging device together according to an embodiment of the disclosure.

FIG. 12 is a conceptual diagram 1200 illustrating a method for measuring a bio-signal of a user by an electronic device and a charging device together according to various embodiments. In various embodiments, the electronic device 201 may measure information related to the body of a user by using at least one sensor (e.g., the sensor module 240 of FIG. 4) included in the electronic device, and measure the information related to the body of the user by using the RF sensor 320 included in the charging device 301 while the electronic device 201 is connected to the charging device 301. Referring to FIG. 12, the electronic device 201 may measure the information related to the body of the user at the same time by using at least one sensor (e.g., the sensor module 240 of FIG. 4) included in the electronic device 201 and the RF sensor 320 included in the charging device 301 together.

While a part (e.g., a finger 1210) of the body of a user 1201 is in contact with the electronic device 201, the electronic device 201 may measure HRV of the user 1201 by using at least one sensor which is in contact with the finger. The electronic device 201 may measure a bio-signal of the user 1201 generated by an RF signal 1220 oscillated from the RF sensor 320 included in the charging device 301. The electronic device 201 may measure various body information of the user in the same amount of time by using two or more sensors together. For example, the electronic device 201 may measure the heart rate variability, blood flow rate, and breathing of the user together, and analyze the measured signal to generate health information of the user.

In various embodiments, while an optical sensor (e.g., the optical sensor 242 or 243 of FIG. 4) among at least one sensor (e.g., the sensor module 240 of FIG. 4) is in contact with the user 1201, the electronic device 201 may measure a first bio-signal of the user by using the optical sensor 242 or 243, receive, from the charging device 301, a second bio-signal of the user obtained through the RF sensor 320, and measure the breathing of the user, based on the first bio-signal and the second bio-signal. For example, while the user's finger is in contact with the optical sensor (e.g., the optical sensor 242 of FIG. 2A) included in the front portion of the electronic device 201, the electronic device may measure a change in heart rate variability (HRV) in response to deep breathing of the user, and determine a stress level of the user, based on the HRV change. The electronic device 201 may determine the stress level, based on oscillation of a time interval between continuous heartbeats and oscillation between continuous instantaneous heart rate (RR interval) in the heart rate variability. The electronic device 201 may determine that the user is in a normal state, when irregular HRV is measured, and may determine that the user is in a tense state or a stress state, when regular HRV is measured. The electronic device 201 may display, on the display 250, the measured breathing of the user together with a breathing guide for relieving stress, based on a result of the determination of the stress level based on the measured breathing, so as to provide the breathing guide to the user. The electronic device 201 may visually display breathing guide data for guiding a deep breathing method to relieve stress.

Figure 13:
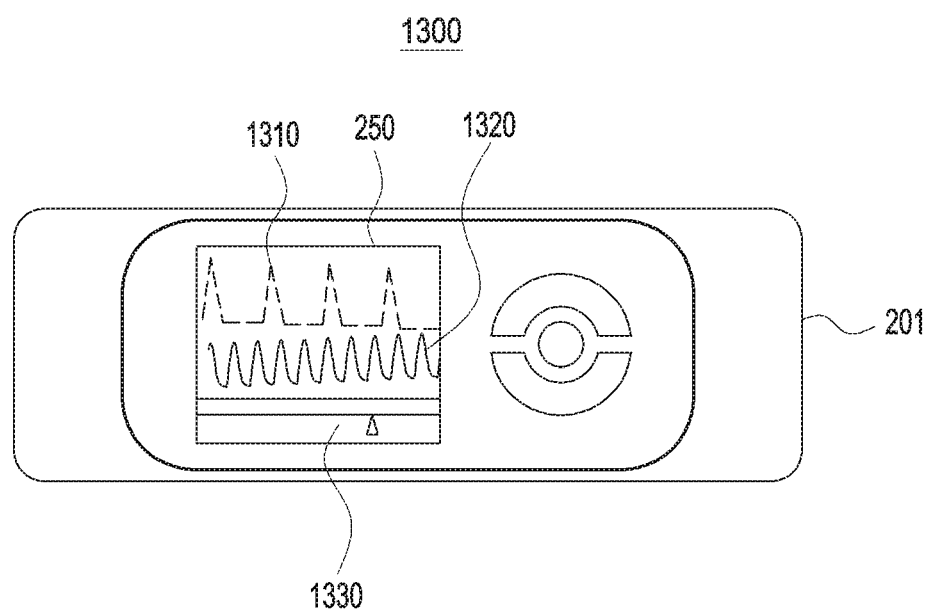
FIG. 13 is an example in which an electronic device provides a breathing guide to a user according to an embodiment of the disclosure.

FIG. 13 is an example 1300 in which an electronic device provides a breathing guide to a user according to various embodiments. In various embodiments, the electronic device 201 may provide reference information together to efficiently provide health information analyzed using a measured bio-signal.

In various embodiments, the electronic device 201 may display, on the display 250, a current breathing and stress index while providing a breathing guide according to an age and gender of a user. For example, the electronic device 201 may display a breathing guide 1310 together with measured breathing data 1320. The electronic device 201 may convert a stress level into a percentage value and visually display 1330 the percentage value on the display 250. The electronic device 201 may provide a stress level to the user, and display a breathing guide, so as to induce the user to perform breathing for stress relief.

According to various embodiments, an electronic device (e.g., the electronic device 101 of FIG. 1 and the electronic device 201 of FIG. 4) may include: a battery (e.g., the battery 189 of FIG. 1); a display (e.g., the display 250 of FIG. 4); at least one sensor (e.g., the sensor module 240 of FIG. 4); an interface (e.g., the interface 210 of FIG. 4); at least one memory (e.g., the memory 260 of FIG. 4); and at least one processor (e.g., the processor 230 of FIG. 4) electrically connected to the display 250, the at least one sensor 240, the interface 210, and the at least one memory 260, wherein the at least one processor 230 is configured to: determine whether a user is wearing the electronic device 201, by using the at least one sensor 240; measure a first bio-signal of the user by using the at least one sensor 240 while the user is wearing the electronic device 201; while the electronic device 201 is connected to a charging device (e.g., the charging device 301 of FIG. 4) including an RF sensor (e.g., the RF sensor 320 of FIG. 4) through the interface 210, drive the RF sensor 320 included in the charging device 301, and measure a second bio-signal of the user, the second bio-signal being generated by an RF signal oscillated from the RF sensor 320; receive at least one of the second bio-signal and power for charging the battery 189 from the charging device 301 through the interface 210; generate health information of the user, at least based on the first bio-signal and the second bio-signal; and display the generated health information on the display 250.

According to an embodiment, the electronic device 201 may identify whether the second bio-signal is measured, and display, through the display 250, whether the second bio-signal is measured. According to an embodiment, in response to the second bio-signal not being measured, the electronic device 201 may provide information for inducing the user to change a location of the charging device 301 or a posture of the user. According to an embodiment, in the electronic device 201, the at least one sensor 240 may include an illuminance sensor (e.g., the illuminance sensor 249 of FIG. 4), measure the brightness around the electronic device 201 through the illuminance sensor 249, and drive the RF sensor 320 when the brightness satisfies a predetermined sleep condition. According to an embodiment, in the electronic device 201, the at least one sensor 240 may include an optical sensor (e.g., the first optical sensor 242 or the second optical sensor 243 of FIG. 4), measure the first bio-signal by using the optical sensor 242 or 243, obtain the second bio-signal obtained through the RF sensor 320, measure breathing of the user, based on the first bio-signal and the second bio-signal, determine a stress level of the user, at least based on the measured breathing, and display, through the display 250, a breathing guide for relieving stress of the user and the measured breathing. According to an embodiment, the electronic device 201 may measure data related to the surrounding environment of the electronic device 201 by using the at least one sensor 240, and generate the health information, further based on the data related to the surrounding environment. According to an embodiment, the electronic device 201 may monitor at least one of the movement or breathing of the user, at least based on the second bio-signal. According to an embodiment, the electronic device 201 may determine a state of the electronic device 201 by using the at least one sensor 240, and drive one of the at least one sensor 240 and the RF sensor 320 of the charging device 301, based on the state of the electronic device 201. According to an embodiment, when it is predicted that the user is in an active state, based on the state of the electronic device 201, the electronic device 201 may drive one of the at least one sensor 240, and when it is predicted that the user is in a sleep state, based on the state of the electronic device 201, the electronic device 201 may drive the RF sensor 320 of the charging device 301. According to an embodiment, the electronic device 201 may change at least one of an RF phase or an antenna direction of the RF sensor 320, based on the measurement strength of the second bio-signal. According to an embodiment, while the electronic device 201 is connected to the charging device 301, when the remaining battery power of the electronic device 201 is less than a predetermined threshold value, the electronic device 201 may control not to drive the RF sensor 320 of the charging device 301. According to an embodiment, the electronic device 201 may further include a communication module (e.g., the communication module 190 of FIG. 1), and transmit the health information to an external electronic device (e.g., the electronic device 102, the electronic device 104, or the server 108 of FIG. 1) by using the communication module 190.

According to an embodiment, a charging device (e.g., the charging device 301 of FIG. 4) may include an RF sensor (e.g., the RF sensor 320 of FIG. 4), a charging circuit (e.g., the charging device 330 of FIG. 4), and an interface (e.g. the interface 310 of FIG. 4). While the charging device is connected to an electronic device (e.g., the electronic device 101 of FIG. 1 or the electronic device 201 of FIG. 4), the charging circuit 330 may supply power to the electronic device 201 and receive a driving signal for driving the RF sensor 320 from the electronic device 201 through the interface 310, the RF sensor 320 may generate an RF signal, in response to the reception of the driving signal, and the RF sensor 320 may measure a user's bio-signal generated by the RF signal and transmit the measured bio-signal to the electronic device 201 through the interface 310. According to an embodiment, the interface 310 of the charging device 301 may come into contact with the interface 210 included in the electronic device 201 to transmit the power and the bio-signal. According to an embodiment, the charging device 301 may further include an LED pointer (e g., the display device 160 of FIG. 1), and, through the interface 310, in response to receiving a driving signal of the LED pointer 160 from the electronic device 201, display an indication line indicating a sensing range of the RF sensor 320 by using the LED pointer 160. According to an embodiment, the charging device 301 may have a cradle structure.

According to various embodiments, a non-transitory computer readable recording medium may store instructions configured to, when executed by a processor (e.g., the processor 120 of FIG. 1 or the processor 230 of FIG. 4), cause the processor 230 to: by using at least one sensor (e.g., the sensor module 240 of FIG. 4) included in an electronic device (e.g., the electronic device 101 of FIG. 1 or the electronic device 201 of FIG. 4), determine whether a user is wearing the electronic device 201, and measure a first bio-signal of the user by using the at least one sensor 240 while the user is wearing the electronic device 201; while the electronic device 201 is connected to a charging device (e.g., the charging device 301 of FIG. 4) including an RF sensor (e.g., the RF sensor 320 of FIG. 4), drive the RF sensor 320 included in the charging device 301, and measure a second bio-signal of the user, the second bio-signal being generated by an RF signal oscillated from the RF sensor 320; receive, from the charging device 301, at least one of the second bio-signal and power for charging a battery (e.g., the battery 189 of FIG. 1) included in the electronic device 201; generate health information of the user, at least based on the first bio-signal and the second bio-signal; and display the generated health information on a display (e.g., the display 250 of FIG. 4).

According to an embodiment, the non-transitory computer readable recording medium may store instructions configured to, when executed, cause the processor 320 to display, through the display 250, whether the second bio-signal is measured, according to a result obtained by identifying whether the second bio-signal is measured.

According to an embodiment, the non-transitory computer readable recording medium may store instructions configured to, when executed, cause the processor 320 to determine a state of the electronic device 201 by using the at least one sensor 240, and drive one of the at least one sensor 240 and the RF sensor 320 of the charging device 301, based on the state of the electronic device 201.

According to an embodiment, the non-transitory computer readable recording medium may store instructions configured to, when executed, cause the processor 320 to transmit the health information to an external electronic device (e.g., the electronic device 102 of FIG. 1, the electronic device 104 of FIG. 1, or the server 108 of FIG. 1) by using a communication module (e.g., the communication module 190 of FIG. 1).

Embodiments disclosed herein are provided merely to describe technical details of the disclosure and to help the understanding of the disclosure, and are not intended to limit the scope of the disclosure. Therefore, it should be construed that the scope of the disclosure includes any change or other various embodiments based on the technical spirit of the disclosure.

The invention claimed is:
1. An electronic device comprising:
   a battery;
   a display;
   at least one sensor;
   an interface;
   and
   at least one processor electrically connected to the display, the at least one sensor, and the interface,
   wherein the at least one processor is configured to:
      determine whether a user is wearing the electronic device, by using the at least one sensor;
      measure a first bio-signal of the user by using the at least one sensor while the user is wearing the electronic device;
      while the electronic device is connected to a charging device including an RF sensor through the interface, control the charging device to obtain a signal being generated using an RF signal outputted from the RF sensor;
      control the charging device to display, using a pointer of the charging device, an indication line indicating a sensing direction of the RF sensor;
      receive the obtained signal from the charging device through the interface;
      generate health information of the user, at least based on the first bio-signal and a second bio-signal corresponding to the received signal; and
      display the generated health information on the display.
2. The electronic device of claim 1,
   wherein the at least one processor is further configured to:
      identify whether the signal is obtained by the charging device, and display, through the display, whether the signal is obtained.
3. The electronic device of claim 2,
   wherein the at least one processor is further configured to:

in response to the signal not being obtained by the charging device, provide information for inducing the user to change a location of the charging device or a posture of the user.

4. The electronic device of claim 1,
wherein the at least one sensor comprises an illuminance sensor, and
wherein the at least one processor is configured to:
measure brightness around the electronic device through the illuminance sensor, and
control the charging device to obtain the signal when the brightness satisfies a predetermined sleep condition.

5. The electronic device of claim 1,
wherein the at least one sensor comprises an optical sensor, and
wherein the at least one processor is configured to:
measure the first bio-signal by using the optical sensor;
measure breathing of the user, based on the first bio-signal and the second bio-signal;
determine a stress level of the user, at least based on the measured breathing; and
display, through the display, a breathing guide for relieving stress of the user and the measured breathing.

6. The electronic device of claim 1,
wherein the at least one processor is configured to:
measure data related to a surrounding environment of the electronic device by using the at least one sensor, and
generate the health information, further based on the data related to the surrounding environment.

7. The electronic device of claim 1,
wherein the at least one processor is further configured to:
monitor at least one of movement or breathing of the user, at least based on the received signal.

8. The electronic device of claim 1,
wherein the at least one processor is configured to:
determine a state of the electronic device by using the at least one sensor, and
drive one of the at least one sensor or the RF sensor of the charging device, based on the state of the electronic device.

9. The electronic device of claim 8,
wherein the at least one processor is configured to:
when it is predicted that the user is in an active state based on the state of the electronic device, drive one of the at least one sensor; and
when it is predicted that the user is in a sleep state based on the state of the electronic device, control the charging device to obtain the signal.

10. The electronic device of claim 1,
wherein the at least one processor is configured to:
change at least one of an RF phase or an antenna direction of the RF sensor, based on a measurement strength of the signal.

11. The electronic device of claim 1,
wherein the at least one processor is configured to:
control the charging device not to obtain the signal, when a remaining battery power of the electronic device is less than a predetermined threshold value while the electronic device is connected to the charging device.

12. The electronic device of claim 1, further comprising a communication module,
wherein the at least one processor is configured to:
transmit the health information to an external electronic device by using the communication module.

13. A non-transitory computer readable recording medium storing instructions, wherein the instructions are configured to, when executed by a processor of an electronic device, cause the electronic device to:
determine whether a user is wearing the electronic device by using at least one sensor included in the electronic device, and measure a first bio-signal of the user by using the at least one sensor while the user is wearing the electronic device;
while the electronic device is connected to a charging device including an RF sensor, control the charging device to obtain a signal being generated using an RF signal outputted from the RF sensor;
control the charging device to display, using a pointer of the charging device, an indication line indicating a sensing direction of the RF sensor;
receive, from the charging device, the obtained signal;
generate health information of the user, at least based on the first bio-signal and a second bio-signal corresponding to the received signal; and
display the generated health information on a display.

14. The non-transitory computer readable recording medium of claim 13, wherein the instructions are further configured to, when executed, cause the processor to:
display, through the display, whether the signal is obtained by the charging device, according to a result obtained by identifying whether the signal is obtained.

15. The non-transitory computer readable recording medium of claim 13, wherein the instructions are further configured to, when executed, cause the processor to:
determine a state of the electronic device by using the at least one sensor; and
control to drive one of the at least one sensor and the RF sensor of the charging device, based on the state of the electronic device.

16. The non-transitory computer readable recording medium of claim 13, wherein the instructions are further configured to, when executed, cause the processor to:
detect that the electronic device is disconnected from the charging device; and
in response to the detection, place the electronic device in standby mode.

* * * * *